United States Patent
Dickerson et al.

(10) Patent No.: US 10,252,975 B2
(45) Date of Patent: Apr. 9, 2019

(54) DERIVATIVES OF 2,2,6-TRIMETHYLCYCLOHEXANE-CARBOXYLATE

(71) Applicant: TAKASAGO INTERNATIONAL CORPORATION, Tokyo (JP)

(72) Inventors: Thalia S. Dickerson, Haskell, NJ (US); Maureen Blandino, North Bergen, NJ (US); Michael E. Lankin, High Bridge, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/906,835

(22) PCT Filed: Jul. 21, 2014

(86) PCT No.: PCT/US2014/047406
§ 371 (c)(1),
(2) Date: Jan. 21, 2016

(87) PCT Pub. No.: WO2015/013184
PCT Pub. Date: Jan. 29, 2015

(65) Prior Publication Data
US 2016/0168074 A1 Jun. 16, 2016

Related U.S. Application Data

(60) Provisional application No. 61/856,794, filed on Jul. 22, 2013.

(51) Int. Cl.
| | | |
|---|---|---|
| C07C 69/75 | (2006.01) | |
| C07C 69/007 | (2006.01) | |
| C07C 323/12 | (2006.01) | |
| C11B 9/00 | (2006.01) | |
| C11D 3/20 | (2006.01) | |
| C11D 3/50 | (2006.01) | |
| A61K 8/37 | (2006.01) | |
| A61Q 13/00 | (2006.01) | |
| A23L 2/56 | (2006.01) | |
| A23G 3/36 | (2006.01) | |
| A23L 27/20 | (2016.01) | |

(52) U.S. Cl.
CPC .............. *C07C 69/75* (2013.01); *A23G 3/36* (2013.01); *A23L 2/56* (2013.01); *A23L 27/203* (2016.08); *C07C 69/007* (2013.01); *C07C 323/12* (2013.01); *C11B 9/0034* (2013.01); *C11D 3/2093* (2013.01); *C11D 3/50* (2013.01); *A23V 2002/00* (2013.01); *C07B 2200/07* (2013.01); *C07C 2601/02* (2017.05); *C07C 2601/08* (2017.05); *C07C 2601/14* (2017.05)

(58) Field of Classification Search
None
See application file for complete search history.

(56) References Cited

U.S. PATENT DOCUMENTS

| | | | |
|---|---|---|---|
| 5,288,702 A * | 2/1994 | Ogura | C07C 61/08 512/24 |
| 7,030,070 B2 | 4/2006 | Sakurai et al. | |
| 2004/0220074 A1 | 11/2004 | Fehr et al. | |
| 2006/0040848 A1 | 2/2006 | Fehr et al. | |
| 2009/0119712 A1 | 5/2009 | Kim et al. | |
| 2009/0181878 A1 | 7/2009 | Fehr et al. | |

FOREIGN PATENT DOCUMENTS

| | | |
|---|---|---|
| CN | 1602184 A | 3/2005 |
| JP | 2012-127012 A | 7/2012 |
| WO | WO 03/049666 A2 | 6/2003 |

OTHER PUBLICATIONS

International Search Report and Written Opinion dated Nov. 5, 2014 in PCT/US2014/047406.
Supplementary European Search Report dated Feb. 9, 2017 in Application No. EP 14828839.
Yamamoto et al., "Olfactory study on optically active citronellyl derivatives," Flavour and Fragrance Journal 19(2):121-133 (2004).

* cited by examiner

*Primary Examiner* — Dennis Heyer
(74) *Attorney, Agent, or Firm* — Baker Botts L.L.P.

(57) ABSTRACT

The present disclosure provides compounds that are derivatives of 2,2,6-trimethylcyclohexanecarboxylate. The disclosed compounds have useful flavor and fragrance characteristics. The present disclosure also provides flavor and fragrance compositions.

18 Claims, No Drawings

DERIVATIVES OF 2,2,6-TRIMETHYLCYCLOHEXANE-CARBOXYLATE

CROSS-REFERENCE TO RELATED APPLICATIONS

This application is a U.S. National Stage Patent Application under 35 U.S.C. § 371 of International Application No. PCT/US2014/047406, filed on Jul. 21, 2014, which claims priority under 35 U.S.C. § 119 to U.S. Provisional Application No. 61/856,794, filed Jul. 22, 2013, the contents of each of which are hereby incorporated by reference in their entireties.

FIELD

The presently disclosed subject matter relates to compounds having uses in the fields of fragrances and flavors, as well as compositions containing such compounds.

BACKGROUND

There is a continuing interest in the preparation of synthetic fragrance and flavor compounds and their use in consumer products. There is a demand, in particular, for compounds with odorant properties similar to damascones.

Damascones (alpha, beta, gamma, and delta isomers) are important odorants in the fragrance and flavor industry, contributing unique fruity, green and floral notes with high diffusion. Damascones structurally contain an α,β-unsaturated ketone group, and thus have been flagged as skin sensitizers. The use of damascones in fragrances and flavors is now highly restricted. The need for damascone replacements is a significant one to the industry.

The compounds of the present invention are derivatives of 2,2,6-trimethylcyclohexane-carboxylate. The carbon skeleton of 2,2,6-trimethylcyclohexane-carboxylate derivatives is similar to the carbon skeleton of the damascones. However, the troublesome α,β-unsaturated ketone group of the damascones is replaced by an ester, anhydride, or acyl carbonate group.

Few esters and other derivatives of 2,2,6-trimethylcyclohexane-carboxylate are known in the literature. The cis methyl ester has been prepared as described in EP920354 and Helv. Chim. Acta. 1973, 2548-2567. The trans methyl ester has been prepared. See J. Am. Chem. Soc. 1942, 385-389. The ethylester has also been described previously in the patent literature. See U.S. Pat. No. 5,288,702. U.S. Pat. No. 4,439,353 discloses fragrant esters of 2,2,5,6-tetramethylcyclohexane carboxylic acid and 6-ethyl-2,2-dimethylcyclohexane carboxylic acid, which have an additional carbon on the cyclohexyl ring moiety as compared to the compounds of the present invention.

The compounds of the presently disclosed subject matter have not been described elsewhere in the literature, with the exception of tert-butyl-2,2,6-trimethylcyclohexane-carboxylate, which is described in JP 2003241366, JP 11029529 and JP 11029528 for uses other than fragrance and/or flavor. In fact, none of the presently disclosed compounds have been described for use as fragrance and/or flavor materials elsewhere in the art. JP 2003241366, JP 11029529 and JP 11029528 disclose tert-butyl-2,2,6-trimethylcyclohexane-carboxylate in racemic form, not in enantioenriched form.

The compounds of the presently disclosed subject matter can be prepared by several synthetic routes. The compounds of the present invention can be prepared from their carboxylic acid precursors by going through an acid chloride intermediate and reacting with the corresponding alcohol or alkyl halide. Shive et al. uses this method to prepare the methyl ester of 2,2,6-trimethylcyclohexane carboxylic acid (J. Am. Chem. Soc. 1942, 385-389).

SUMMARY

The presently disclosed subject matter provides compounds, flavor compositions, and fragrance compositions.

In certain embodiments, the present disclosure provides compounds of Formula (I):

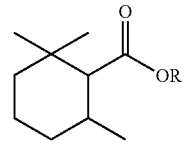

(I)

wherein R is an unsubstituted or substituted $C_3$-$C_8$ straight chain alkyl, an unsubstituted or substituted $C_3$-$C_8$ branched chain alkyl, an unsubstituted or substituted $C_3$-$C_8$ straight chain alkenyl, an unsubstituted or substituted $C_3$-$C_8$ branched chain alkenyl, an unsubstituted or substituted $C_3$-$C_8$ straight chain alkynyl, an unsubstituted or substituted $C_3$-$C_8$ branched chain alkynyl, an unsubstituted or substituted $C_3$-$C_8$ cycloalkyl, an unsubstituted or substituted $C_3$-$C_8$ cycloalkenyl, an unsubstituted or substituted $C_2$-$C_8$ alkylalkoxy, an unsubstituted or substituted $C_2$-$C_8$ alkyl (alkylthio), an unsubstituted or substituted aryl, an unsubstituted or substituted benzyl, an unsubstituted or substituted naphthyl, an unsubstituted or substituted nonaromatic heterocyclic, an unsubstituted or substituted heteroaryl, an unsubstituted or substituted $C_1$-$C_8$ acyl, or an unsubstituted or substituted carboxy, including stereoisomers and mixtures thereof.

In certain embodiments, the present disclosure provides compounds of Formula (Ib):

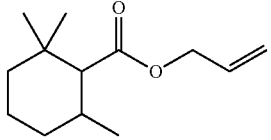

(Ib)

including stereoisomers and mixtures thereof. Compounds of Formula (Ib) are compounds of Formula (I) in which R is allyl. In certain embodiments, the compound is (1R,6S)-allyl 2,2,6-trimethylcyclohexane-carboxylate.

In certain embodiments, the present disclosure provides compounds of Formula (Ic):

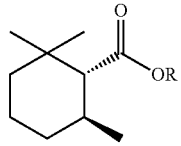

(Ic)

wherein R is an unsubstituted or substituted $C_3$-$C_8$ straight chain alkyl, an unsubstituted or substituted $C_3$-$C_8$ branched chain alkyl, an unsubstituted or substituted $C_3$-$C_8$ straight chain alkenyl, an unsubstituted or substituted $C_3$-$C_8$ branched chain alkenyl, an unsubstituted or substituted $C_3$-$C_8$ straight chain alkynyl, an unsubstituted or substituted $C_3$-$C_8$ branched chain alkynyl, an unsubstituted or substituted $C_3$-$C_8$ cycloalkyl, an unsubstituted or substituted $C_3$-$C_8$ cycloalkenyl, an unsubstituted or substituted $C_2$-$C_8$ alkylalkoxy, an unsubstituted or substituted $C_2$-$C_5$ alkyl (alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted $C_1$-$C_8$ acyl, or an unsubstituted or substituted carboxy, including mixtures thereof.

In certain embodiments, the present disclosure provides compounds of Formula (Id):

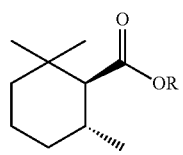

(Id)

wherein R is an unsubstituted or substituted $C_3$-$C_8$ straight chain alkyl, an unsubstituted or substituted $C_3$-$C_8$ branched chain alkyl, an unsubstituted or substituted $C_3$-$C_8$ straight chain alkenyl, an unsubstituted or substituted $C_3$-$C_8$ branched chain alkenyl, an unsubstituted or substituted $C_3$-$C_8$ straight chain alkynyl, an unsubstituted or substituted $C_3$-$C_8$ branched chain alkynyl, an unsubstituted or substituted $C_3$-$C_8$ cycloalkyl, an unsubstituted or substituted $C_3$-$C_8$ cycloalkenyl, an unsubstituted or substituted $C_2$-$C_8$ alkylalkoxy, an unsubstituted or substituted $C_2$-$C_8$ alkyl (alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted $C_1$-$C_8$ acyl, or an unsubstituted or substituted carboxy, including mixtures thereof.

The present disclosure also provides flavor compositions. An exemplary flavor composition includes one or more compounds of Formula (I), as defined above. The composition can further include one or more additional flavor components. The flavor composition can include (1R,6S)-allyl 2,2,6-trimethylcyclohexanecarboxylate. In certain embodiments, the flavor composition can be incorporated into a product, which can be one or more foods, beverages, confectionaries, oral care products, pharmaceuticals, and/or gelatinous materials. The beverage can be one or more alcoholic beverages, soft drinks, juices, teas, and/or flavored waters. The confectionary can be one or more candies and/or gums. The oral care product can be one or more toothpastes and/or mouthwashes.

The present disclosure also provides fragrance compositions. An exemplary fragrance composition includes one or more compounds of Formula (I), as defined above. The composition can further include one or more additional fragrance components. The fragrance composition can include (1R,6S)-allyl 2,2,6-trimethylcyclohexanecarboxylate. In certain embodiments, the fragrance composition can be incorporated into a product, which can be one or more perfumes, colognes, air fresheners or other air care compositions, candles, personal care products, cosmetics, detergents, fabric care products, and/or household cleaning agents. The personal care product can be one or more soaps, deodorants, shampoos, conditioners, shower gels, and/or shaving lotions. The cosmetic can be one or more creams, lotions, ointments, oils, sprays, powders, gels, polishes, and/or lipsticks.

DETAILED DESCRIPTION

While both terms "fragrance" and "flavor" are used herein, it should be understood that compounds that can have beneficial fragrance properties can also have beneficial flavor properties, and vice versa. Accordingly, the terms "fragrance" and "flavor" are not mutually exclusive but instead can each encompass both fragrance and flavor. A "fragrance composition" or a "flavor composition" can have both fragrance and flavor properties and can be synonymous with a "flavor and fragrance composition." Fragrance can also be known as aroma.

As used herein, the term "skin sensitizer" refers to substances or materials that can induce inflammation, itchiness, and/or other allergic or immune responses upon skin contact.

As used herein, the term "enantioenriched" refers to a sample of a chiral compound that contains more of one enantiomer than the other. For example, an enantioenriched sample of a compound can contain 60% of one enantiomer and 40% of the other, or 70% of one enantiomer and 30% of the other, or 80% of one enantiomer and 20% of the other, or 90% of one enantiomer and 10% of the other. Enantioenriched samples of a compound can be distinguished from racemic samples of a compound, which contain equal quantities (50:50 mixtures) of the enantiomers.

As used herein, the term "alkyl" refers to saturated aliphatic groups. Alkyl groups can be straight chain (e.g., ethyl, n-propyl, n-butyl) or branched chain (e.g., i-propyl, s-butyl).

As used herein, the term "alkenyl" refers to an unsaturated aliphatic group having at least one carbon-carbon double bond (C=C). Alkenyl groups can be straight chain (e.g., allyl) or branched (e.g., prenyl).

As used herein, the term "alkynyl" refers to an unsaturated aliphatic group having at least one carbon-carbon triple bond (C≡C). Alkynyl groups can be straight chain (e.g., propargyl) or branched.

As used herein, the term "cycloalkyl" refers to a saturated aliphatic carbon-based cyclic group. Cycloalkyl groups can include one ring or more than one ring. By way of non-limiting example, cycloalkyl groups can include cyclopropyl, cyclobutyl, cyclopentyl, cyclohexyl, cycloheptyl, and cyclooctyl.

As used herein, the term "cycloalkenyl" refers to an unsaturated aliphatic carbon-based cyclic group having at least one carbon-carbon double bond (C=C). Cycloalkenyl groups can include one ring or more than one ring.

As used herein, the term "alkylalkoxy" refers to an alkyl group that is further substituted with one or more alkoxy groups.

As used herein, the term "alkoxy" refers to a moiety of formula —$OR^1$, wherein $R^1$ is an alkyl or cycloalkyl group.

As used herein, the term "alkyl(alkylthio)" refers to an alkyl group that is further substituted with one or more alkylthio groups.

As used herein, the term "alkylthio" refers to a moiety of formula —$SR^2$, wherein $R^2$ is an alkyl or cycloalkyl group.

As used herein, the term "aryl" refers to an unsaturated, aromatic carbon-based cyclic group. Aryl groups can include one ring or more than one ring. By way of non-limiting example, aryl groups can include phenyl, naphthyl, tolyl, and xylyl groups.

As used herein, the term "benzyl" refers to a moiety of formula —CH$_2$Ph.

As used herein, the term "nonaromatic heterocyclic" refers to a saturated or unsaturated nonaromatic group that includes both carbon atoms and heteroatoms. Nonaromatic heterocyclic groups can include one ring or more than one ring. In certain embodiments, nonaromatic heterocyclic groups can be monocyclic 3-, 4-, 5-, 6-, 7-, or 8-membered rings that contain 1, 2, 3, 4, 5, or 6 heteroatoms. In certain embodiments, nonaromatic heterocyclic groups can be bicyclic ring systems. The heteroatoms can be N, O, and/or S. By way of non-limiting example, nonaromatic heterocyclic groups can include piperazinyl, morpholinyl, pyrrolidinyl, oxetanyl, pyrazolinyl, imidazolinyl, imidazolidinyl, oxazolidinyl, isoxazolinyl, thiazolidinyl, isothiazolidinyl, dihydrofuryl, tetrahydrofuryl, pyranyl, dihydropyranyl, tetrahydropyranyl, piperidinyl, 2-oxopiperazinyl, 2-oxopiperidinyl, 2-oxopyrrolidinyl, 2-oxazepinyl, azepinyl, hexahydroazepinyl, tetrahydrothiopyranyl, thiomorpholinyl, dioxanyl, isothiazolidinyl, thietanyl, thiiranyl, and the like. The heterocyclic group can be bound at any point along the ring suitable for substitution, i.e., at the 1-, 2-, 3-, 4-, or 5-position of a 5-membered ring or at the 1-, 2-, 3-, 4-, 5-, or 6-position of a 6-membered ring.

As used herein, the term "heteroaryl" refers to an unsaturated, aromatic cyclic group that includes both carbon atoms and heteroatoms. Heteroaryl groups can include one ring or more than one ring. In certain embodiments, heteroaryl groups can be monocyclic 5- or 6-membered rings that include 1, 2, 3, or 4 heteroatoms. The heteroatoms can be N, O, and/or S. By way of non-limiting example, heteroaryl groups can include pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, and benzothiophenyl groups. The heteroaryl group can be bound at any point along the ring suitable for substitution, i.e., at the 1-, 2-, 3-, 4-, or 5-position of a 5-membered ring or at the 1-, 2-, 3-, 4-, 5-, or 6-position of a 6-membered ring.

As used herein, the term "acyl" refers to a moiety of formula —C(O)R$^3$, wherein R$^3$ is an alkyl, cycloalkyl, alkenyl, cycloalkenyl, alkynyl, aryl, or benzyl group.

As used herein, the term "carboxy" refers to a moiety of formula —C(O)OR$^4$, wherein R$^4$ is an alkyl, cycloalkyl, alkenyl, cycloalkenyl, alkynyl, aryl, or benzyl group.

As used herein, the term "stereoisomer(s)" refers to any possible enantiomers, diastereomers, cis-/trans-isomers and/or E-/Z-isomers.

As used herein, the term "substituted" means that a group can be further substituted by replacement of one or more hydrogen radicals with one or more groups selected from oxygen, nitrogen, sulfur, alkyl, alkenyl, alkynyl, aryl, halo, haloalkyl, haloalkenyl, haloalkynyl, haloaryl, hydroxy, alkoxy, carboxy, haloalkoxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulfonyl, arylsulfonyl, alkylsulfonylamino, arylsulfonylamino, alkylsulfonyloxy, arylsulfonyloxy, heterocyclyl, heterocycloxy, helerocyclylamino, haloheterocyclyl, alkylsulfenyl, arylsulfenyl, carboalkoxy, carboaryloxy, mercapto, alkylthio, arylthio, acylthio and the like.

In certain embodiments, the present disclosure provides compounds of Formula (I):

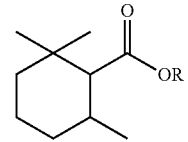

(I)

wherein R is an unsubstituted or substituted C$_3$-C$_8$ straight chain alkyl, an unsubstituted or substituted C$_3$-C$_8$ branched chain alkyl, an unsubstituted or substituted C$_3$-C$_8$ straight chain alkenyl, an unsubstituted or substituted C$_3$-C$_8$ branched chain alkenyl, an unsubstituted or substituted C$_3$-C$_8$ straight chain alkynyl, an unsubstituted or substituted C$_3$-C$_8$ branched chain alkynyl, an unsubstituted or substituted C$_3$-C$_8$ cycloalkyl, an unsubstituted or substituted C$_3$-C$_8$ cycloalkenyl, an unsubstituted or substituted C$_2$-C$_8$ alkylalkoxy, an unsubstituted or substituted C$_2$-C$_8$ alkyl (alkylthio), an unsubstituted or substituted aryl, an unsubstituted or substituted benzyl, an unsubstituted or substituted naphthyl, an unsubstituted or substituted piperazinyl, an unsubstituted or substituted morpholinyl, an unsubstituted or substituted heteroaryl, an unsubstituted or substituted C$_1$-C$_8$ acyl, or an unsubstituted or substituted carboxy, including stereoisomers and mixtures thereof.

In certain embodiments, the present disclosure provides compounds of Formula (Ic):

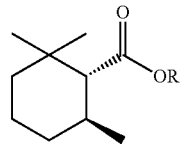

(Ic)

wherein R is an unsubstituted or substituted C$_3$-C$_8$ straight chain alkyl, an unsubstituted or substituted C$_3$-C$_8$ branched chain alkyl, an unsubstituted or substituted C$_3$-C$_8$ straight chain alkenyl, an unsubstituted or substituted C$_3$-C$_8$ branched chain alkenyl, an unsubstituted or substituted C$_3$-C$_8$ straight chain alkynyl, an unsubstituted or substituted C$_3$-C$_8$ branched chain alkynyl, an unsubstituted or substituted C$_3$-C$_8$ cycloalkyl, an unsubstituted or substituted C$_3$-C$_8$ cycloalkenyl, an unsubstituted or substituted C$_2$-C$_8$ alkylalkoxy, an unsubstituted or substituted C$_2$-C$_8$ alkyl (alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C$_1$-C$_8$ acyl, or an unsubstituted or substituted carboxy, including mixtures thereof.

In certain embodiments, the present disclosure provides compounds of Formula (Id):

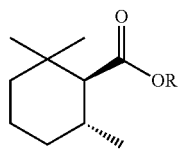

(Id)

wherein R is an unsubstituted or substituted $C_3$-$C_8$ straight chain alkyl, an unsubstituted or substituted $C_3$-$C_8$ branched chain alkyl, an unsubstituted or substituted $C_3$-$C_8$ straight chain alkenyl, an unsubstituted or substituted $C_3$-$C_8$ branched chain alkenyl, an unsubstituted or substituted $C_3$-$C_8$ straight chain alkynyl, an unsubstituted or substituted $C_3$-$C_8$ branched chain alkynyl, an unsubstituted or substituted $C_3$-$C_8$ cycloalkyl, an unsubstituted or substituted $C_3$-$C_8$ cycloalkenyl, an unsubstituted or substituted $C_2$-$C_8$ alkylalkoxy, an unsubstituted or substituted $C_2$-$C_8$ alkyl (alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted $C_1$-$C_8$ acyl, or an unsubstituted or substituted carboxy, including mixtures thereof.

Compounds of Formula (I) include compounds of Formulae (Ic) and (Id). That is, compounds of Formulae (Ic) and (Id) are compounds of compounds of Formula (I) with defined stereochemistry. Formulae (Ic) and (Id) are subsets of Formula (I). Compounds of Formula (Ic) have (1R,6S) stereochemistry while compounds of Formula (Id) have (1S,6R) stereochemistry. Compounds of Formulae (Ic) and (Id) are encompassed by Formula (I), and all preparations, combinations, formulations, compositions, and methods of use of compounds of Formula (I) can include compounds of Formulae (Ie) and/or (Id). As noted below, compounds of Formulae (Ic) and (Id) can be prepared in enantioenriched form. That is, the present disclosure provides preparations of compounds of Formula (Ic) enriched in the (1R,6S)-enantiomer as compared to the (1S,6R)-enantiomer as well as preparation of compounds of Formula (Id) enriched in the (1S,6R)-enantiomer as compared to the (1R,6S)-enantiomer.

The compounds of the present disclosure can be used singly or in combination. Combinations or mixtures of compounds of Formula (I) can include two, three, four, or more compounds of Formula (I). Compounds of Formula (I) can be colorless or nearly colorless liquids that are compatible with other fragrance and flavor compounds.

In certain embodiments, the compound of Formula (I) is a compound wherein R is an unsubstituted or substituted $C_3$-$C_8$ branched chain alkyl, an unsubstituted or substituted $C_3$-$C_8$ straight chain alkenyl, an unsubstituted or substituted $C_3$-$C_8$ straight chain alkynyl, an unsubstituted or substituted $C_3$-$C_8$ cycloalkyl, or an unsubstituted or substituted $C_2$-$C_8$ alkyl(alkylthio) group.

In certain embodiments, the present disclosure provides compounds of Formula (Ib):

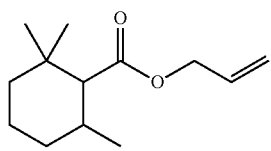

(Ib)

including stereoisomers and mixtures thereof. Compounds of Formula (Ib) are compounds of Formula (I) in which R is allyl. In certain embodiments, the compound is (1R,6S)-allyl 2,2,6-trimethylcyclohexanecarboxylate.

Compounds of Formula (I) can be prepared according to procedures known in the art. By way of non-limiting example, compounds of Formula (I) can be prepared by derivatization of 2,2,6-trimethylcyclohexanecarboxylic acid, e.g. by esterification or acylation. Esterification and/or acylation of 2,2,6-trimethylcyclohexanecarboxylic acid can be performed according to procedures known in the art. For example, as described in the Examples of the present disclosure, 2,2,6-trimethylcyclohexanecarboxylic acid can be converted to an acid chloride intermediate, and the acid chloride intermediate can undergo further reaction to provide compounds of Formula (I). 2,2,6-Trimethylcyclohexanecarboxylic acid can be converted to other reactive intermediates—e.g., an acid bromide, an activated ester, such as a hydroxybenzotriazole (HOBt) ester, or an activated anhydride, such as a Yamaguchi anhydride—which can undergo further reaction to provide compounds of Formula (I). 2,2,6-Trimethylcyclohexanecarboxylic acid can be directly converted to compounds of Formula (I), e.g., through esterification with an alcohol under Fisher esterification conditions, or through reaction with an acyl halide intermediate to provide an anhydride or acyl carbonate derivative. Compounds of Formula (I) can be prepared according to general procedures disclosed in U.S. Pat. No. 5,288,702, the synthetic procedures of which are hereby incorporated by reference. 2,2,6-Trimethylcyclohexanecarboxylic acid, including both the (1R,6S)- and (1S,6R)-isomers thereof, can be prepared according to the synthetic procedure of U.S. Pat. No. 5,288,702, which is hereby incorporated by reference.

The present disclosure provides flavor compositions. An exemplary flavor composition can include one or more compounds of Formula (I), as defined above. The composition can further include one or more additional flavor components. The additional flavor components can be flavor and/or fragrance compounds known in the art. For example, additional flavor components can include, but are not limited to, various natural flavors, artificial flavors, acids, bases, amino acids, salts, sweeteners, esters, terpenes, and aromatics. In certain embodiments, the flavor composition can be incorporated into a product, which can be one or more foods, beverages, confectionaries, oral care products, pharmaceuticals, and/or gelatinous materials. The food can be one or more baked goods, snacks, dairy products, and/or desserts. The beverage can be one or more alcoholic beverages, soft drinks, juices, teas, and/or flavored waters. The confectionary can be one or more candies and/or gums. The oral care product can be one or more toothpastes and/or mouthwashes. In certain embodiments, the concentration of the one or more compounds of Formula (I) in a flavor composition can range from 0.001% to 5%, from 0.001% to 0.1%, from 0.005% to 0.1%, from 0.001% to 1%, from 0.005% to 1%, from 0.01% to 1%, from 0.01% to 5%, from 0.05% to 5%, from 0.1% to 5%, or from 1% to 5%, by weight. In certain embodiments, the concentration of the one or more compounds of Formula (I) in a flavor composition can range from 0.01% to 0.5%, from 0.01% to 0.4%, from 0.01% to 0.3%, from 0.01% to 0.2%, from 0.01% to 0.1%, or from 0.01% to 0.05%, by weight.

The present disclosure provides fragrance compositions. An exemplary fragrance composition includes one or more compounds of Formula (I), as defined above. The composition can further include one or more additional fragrance components. The additional fragrance components can be flavor and/or fragrance compounds known in the art. For example, additional fragrance components can include, but are not limited to, various esters, terpenes, aldehydes, ketones, ethers, nitriles, essential oils, and other aromatics. In certain embodiments, the fragrance composition can be incorporated into a product, which can be one or more perfumes, colognes, air fresheners, candles, personal care products, cosmetics, detergents, fabric care products, and/or household cleaning agents. The personal care product can be one or more soaps, deodorants, shampoos, conditioners, shower gels, and/or shaving lotions. The cosmetic can be one or more creams, lotions, ointments, oils, sprays, powders, gels, polishes, and/or lipsticks. Compounds of Formula (I) can be particularly valuable in a fragrance composition for imparting floral, fruity, fresh, berry notes to a composition. In certain embodiments, the concentration of the one or more compounds of Formula (I) in a fragrance composition can range from 0.01% to 50%, from 0.01% to 1%, from 0.05% to 1%, from 0.01% to 10%, from 0.05% to 10%, from 0.1% to 10%, from 0.1% to 50%, from 0.5% to 50%, from 1% to 50%, or from 10% to 50%, by weight. In certain embodiments, the concentration of the one or more compounds of Formula (I) in a fragrance composition can range from 0.1% to 5.0%, from 0.1% to 4%, from 0.1% from 3%, from 0.1% to 2%, from 0.1% to 1%, or from 0.1% to 0.5%, by weight.

A fragrance or flavor composition can include (1R,6S)-allyl 2,2,6-trimethylcyclohexanecarboxylate. (1R,6S)-allyl 2,2,6-trimethylcyclohexanecarboxylate can have beneficial properties when included in a fragrance or flavor composition. For example, (1R,6S)-allyl 2,2,6-trimethylcyclohexanecarboxylate can have a damascone-like or rose-like fragrance or aroma and can impart a damascone-like or rose-like character to a composition. Surprisingly, it has also been found that (1R,6S)-allyl 2,2,6-trimethylcyclohexanecarboxylate can also give a unique fruity floral character to a composition, with nuances of berry and nectarine distinct from a damascone- or rose-like fragrance or aroma. Unlike damascones, (1R,6S)-allyl 2,2,6-trimethylcyclohexanecarboxylate does not contain an $\alpha,\beta$-unsaturated ketone and can present reduced risk as a skin sensitizer as compared to damascones. In certain embodiments, the concentration of (1R,6S)-allyl 2,2,6-trimethylcyclohexanecarboxylate in a fragrance composition can range from 0.01% to 50%, from 0.01% to 1%, from 0.05% to 1%, from 0.01% to 10%, from 0.05% to 10%, from 0.1% to 10%, from 0.1% to 50%, from 0.5% to 50%, from 1% to 50%, or from 10% to 50%, by weight. In certain preferred embodiments, concentrations of (1R,6S)-allyl 2,2,6-trimethylcyclohexanecarboxylate in a fragrance composition can range from 0.1% to 5.0%, from 0.1% to 4%, from 0.1% from 3%, from 0.1% to 2%, from 0.1% to 1%, or from 0.1% to 0.5%, by weight. In certain embodiments, the concentration of (1R,6S)-allyl 2,2,6-trimethylcyclohexanecarboxylate in a flavor composition can range from 0.001% to 5%, from 0.001% to 0.1%, from 0.005% to 0.1%, from 0.001% to 1%, from 0.005% to 1%, from 0.01% to 1%, from 0.01% to 5%, from 0.05% to 5%, from 0.1% to 5%, or from 1% to 5%, by weight. In certain preferred embodiments, concentrations of (1R,6S)-allyl 2,2,6-trimethylcyclohexanecarboxylate in a flavor composition can range from 0.01% to 0.5%, from 0.01% to 0.4%, from 0.01% to 0.3%, from 0.01% to 0.2%, from 0.01% to 0.1%, or from 0.01% to 0.05%, by weight.

Compounds of Formula I can have certain advantages over damascones. In certain embodiments, compounds of Formula I can have improved stability as compared to damascones. Compounds of Formula I can have improved chemical stability, e.g., improved stability under oxidizing conditions, as compared to damascones. Compounds of Formula I can have improved stability in the presence of chemical bleaches, including hypochlorite salts, as compared to damascones, and can cause reduced degradation of chemical bleaches. For example, (1R,6S)-allyl 2,2,6-trimethylcyclohexane-carboxylate can have improved stability to sodium hypochlorite (NaClO) as compared to delta-damascone, as described in Example 15, Compounds of Formula I can have certain advantageous properties when combined in flavor or fragrance compositions with one or more additional fragrance components. As noted in the Examples below, compounds of Formula I can be effective in producing appealing flavors and/or fragrances when combined with other flavor and fragrance compounds, including other compounds with floral and/or fruity characteristics.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compounds and compositions of the disclosed subject matter without departing from the spirit or scope of the disclosed subject matter. Thus, it is intended that the disclosed subject matter include modifications and variations that are within the scope of the appended claims and their equivalents.

EXAMPLES

The following examples are merely illustrative of specific embodiments of the presently disclosed subject matter and should not be construed to be limiting. Abbreviations have the usual meaning in the art. The temperatures are indicated in degrees centigrade (° C.). The NMR spectral data were recorded in CDCl$_3$ with a 400 MHz machine for $^1$H and $^{13}$C. The chemical displacements are indicated in ppm with respect to TMS as the standard.

Odor evaluations (e.g., floral, fruity, minty) were made by a panel of expert perfumers or at least one expert perfumer.

As used in the examples below, "(1R,6S)-2,2,6-trimethylcyclohexanecarboxylic acid" is an enantioenriched sample of the compound and contains 90% (1R,6S)-2,2,6-trimethylcyclohexanecarboxylic acid and 10% of the (1S,6R)-enantiomer. As used in the examples below, "(1S,6R)-2,2,6-trimethylcyclohexanecarboxylic acid" is an enantioenriched sample of the compound and contains 90% (1S,6R)-2,2,6-trimethylcyclohexanecarboxylic acid and 10% of the (1R,6S)-enantiomer.

Example 1a: Synthesis of (1R,6S)-2,2,6-trimethylcyclohexanecarbonyl chloride ("(1R,6S)-isomer of the acid chloride intermediate")

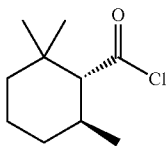

To a cold solution of (1R,6S)-2,2,6-trimethylcyclohexanecarboxylic acid (1 eq), in dichloromethane (200 mL) at 0° C., was added thionyl chloride (1.2 eq) drop wise over 15 mins. After addition, the reaction mixture was warmed to room temperature then heated to 50° C. for 1.5 hr. The mixture was cooled to room temperature and concentrated under reduced vacuum. The crude material was taken to the next step immediately.

Example 1b: Synthesis of (1S,6R)-2,2,6-trimethylcyclohexanecarbonyl chloride ("the (1S,6R)-isomer of the acid chloride intermediate")

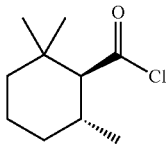

To a cold solution of (1R,6S)-2,2,6-trimethylcyclohexanecarboxylic acid (1 eq) in dichloromethane (200 mL) at 0° C., was added thionyl chloride (1.2 eq) drop wise over 15 mins. After addition, the reaction mixture was warmed to room temperature then heated to 50° C. for 1.5 hr. The mixture was cooled to room temperature and concentrated under reduced vacuum. The crude material was taken to the next step immediately.

Example 2: Synthesis of (1R,6S)-allyl 2,16-trimethlcyclohexanecarboxylate

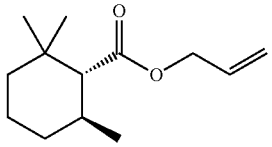

To a cold flask containing the (1R,6S)-isomer of the acid chloride intermediate at 0° C., was added allyl chloride (10.5 eq; used as solvent) drop wise over 20 mins. After addition, the mixture was heated to 75° C. where it remained overnight (GC showed crude reaction with ~98% purity). The material was diluted with ethyl acetate and washed with 5% $Na_2CO_3$ (2×) and water (2×). The aqueous layer was back extracted with ethyl acetate (1×). The organics were combined, dried over $MgSO_4$, filtered and concentrated under reduced pressure. The crude material was purified via fractional distillation (bath=70-71° C., bulb=56-60° C., vacuum press.=0.18-0.9 Torr) (yield 67.9%). $^1H$ NMR (400 MHz, $CDCl_3$) δ ppm 0.88 (m, 10H) 1.15 (m, 1H) 1.45 (m, 3H) 1.70 (dd, 1H) 1.83 (n, 2H) 4.55 (m, 2H) 5.21 (d, 1H) 5.32 (n, 1H) 5.91 (qd, 1H). $^{13}C$ NMR (101 MHz, $CDCl_3$) δ ppm 20.98, 21.23, 21.74, 30.29, 31.41, 34.60, 41.27, 60.91, 64.51, 118.27, 132.60, 174.27. Odor descriptors: Fruity, pineapple, juicy, apple, berry, fresh, damascone, ethyl safranate, exotic.

Example 3: Synthesis of (1S,6R)-allyl 2,2,6-trimethylcyclohexanecarboxylate

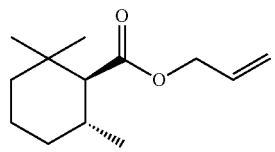

To a cold flask containing the (1S,6R)-isomer of the acid chloride intermediate at 0° C., was added allyl chloride (10.5 eq; used as solvent) drop wise over 20 mins. After addition, the mixture was heated to 75° C. where it remained overnight (GC showed crude reaction with ~98% purity). The material was diluted with ethyl acetate and washed with 5% $Na_2CO_3$ (2×) and water (2×). The aqueous layer was back extracted with ethyl acetate (1×). The organics were combined, dried over $MgSO_4$, filtered and concentrated under reduced pressure. The crude material was purified via silica gel eluted with 0-2% Ethyl Acetate/Hexanes mixture (53.9% yield). $^1H$ NMR (400 MHz, $CDCl_3$) δ ppm 0.87 (m, 10H) 1.15 (ddd, 1H) 1.44 (m, 3H) 1.70 (m, 1H) 1.83 (m, 2H) 4.55 (m, 2H) 5.21 (dd, 1H) 5.32 (m, 1H) 5.91 (m, 1H). $^{13}C$ NMR (101 MHz, $CDCl_3$) δ ppm 20.98, 21.24, 21.74, 30.29, 31.42, 34.60, 41.27, 60.91, 64.52, 118.28, 132.60, 174.28. Odor descriptors: floral, fruity, minty, apple, plum.

Example 4: Synthesis of (1R,6S)-3-(methylthio)hexyl 2,2,6-trimethylcyclohexanecarboxylate

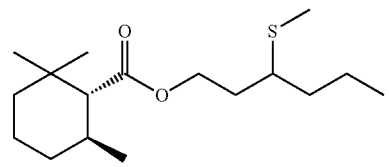 [SMILES: CCCC(CCOC(=O)[C@@H]1[C@@H](C)CCCC1(C)C)SC]

To a cold flask containing the (1R,6S)-isomer of the acid chloride intermediate at 0° C., was added 3-methylthio-1-hexanol (10.5 eq; used as solvent) drop wise over 20 mins. After addition, the mixture was warmed to room temperature where it remained overnight. The material was diluted with ethyl acetate and washed with 5% $Na_2CO_3$ (1×) and water (1×). The aqueous layer was back extracted with ethyl acetate (1×). The organics were combined and washed with brine (1×). The organics were separated and dried over $MgSO_4$, filtered and concentrated under reduced pressure. The crude material was purified via silica gel eluted with 0-3% Ethyl Acetate/Hexanes mixture (53.9% yield). $^1H$ NMR (400 MHz, $CDCl_3$) δ ppm 0.86 (m, 13H) 1.12 (m, 1H)

1.44 (m, 7H) 1.80 (m, 5H) 2.00 (m, 3H) 2.58 (m, 1H) 4.21 (m, 2H). $^{13}$C NMR (101 MHz, CDCl$_3$) δ ppm 12.36, 12.50, 13.98, 20.09, 21.00, 21.24, 21.74, 30.24, 31.43, 33.21, 33.35, 34.58, 36.54, 36.59, 41.24, 43.05, 43.15, 60.97, 61.64, 76.79, 77.11, 77.43, 174.57. Odor descriptors: fresh crushed garlic.

Example 5: Synthesis of (1R,6S)—((Z)-hex-3-enyl) 2,2,6-tritmethylcyclohexanecarboxylate

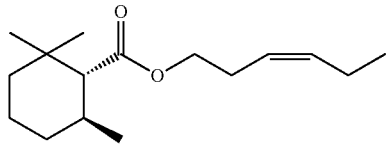 [SMILES: CC/C=C\CCOC(=O)[C@@H]1[C@@H](C)CCCC1(C)C]

To a cold flask containing the (1R,6S)-isomer of the acid chloride intermediate at 0° C., was added cis-3-hexenol (10.5 eq; used as solvent) drop wise over 20 mins. After addition, the mixture was warmed to room temperature where it remained overnight. The material was diluted with ethyl acetate and washed with 5% Na$_2$CO$_3$ (1×) and water (1×). The aqueous layer was back extracted with ethyl acetate (1×). The organics were combined and washed with brine (1×). The organics were separated and dried over MgSO$_4$, filtered and concentrated under reduced pressure. The crude material was purified via silica gel eluted with 0-2% Ethyl Acetate/Hexanes mixture (70.8% yield). $^1$H NMR (400 MHz, CDCl$_3$) δ ppm 0.87 (m, 13H) 1.13 (m, 1H) 1.42 (m, 3H) 1.75 (m, 3H) 2.03 (m, 2H) 2.36 (q, 2H) 4.05 (m, 2H) 5.31 (m, 1H) 5.47 (m, 1H). $^{13}$C NMR (101 MHz, CDCl$_3$) δ ppm 14.30, 20.71, 21.00, 21.26, 21.75, 26.94, 30.22, 31.42, 34.61, 41.29, 60.96, 63.40, 124.10, 134.42, 174.65. Odor descriptors: weak, pineapple, fruity, sweet, orange juice pulp, waxy.

Example 6: Synthesis of (1R,6S)-prop-2-trimethylcyclohexanecarboxylate

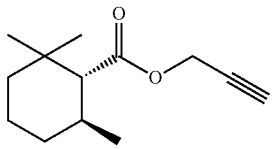

To a cold flask containing the (1R,6S)-isomer of the acid chloride intermediate at 0° C., was added propargyl alcohol (10.5 eq; used as solvent) drop wise over 20 mins. After addition, the mixture was warmed to room temperature where it remained overnight. The material was diluted with ethyl acetate and washed with 5% Na$_2$CO$_3$ (1×) and water (1×). The aqueous layer was back extracted with ethyl acetate (1×). The organics were combined and washed with brine (1×). The organics were separated and dried over MgSO$_4$, filtered and concentrated under reduced pressure. The crude material was purified via fractional distillation (55.4% yield). $^1$H NMR (400 MHz, CDCl$_3$) δ ppm 0.88 (m, 10H) 1.14 (m, 1H) 1.43 (m, 3H) 1.70 (m, 1H) 1.85 (m, 2H) 2.42 (t, 1H) 4.65 (m, 2H). $^{13}$C NMR (101 MHz, CDCl$_3$) δ ppm 20.90, 21.17, 21.68, 30.36, 31.33, 34.54, 41.22, 51.09, 60.63, 74.52, 173.79. Odor descriptors: fruity, apple, plum, wine.

Example 7: Synthesis of (1R,6S)-2-(ethylthio)ethyl 2,2,6-trimethylcyclohexanecarboxylate

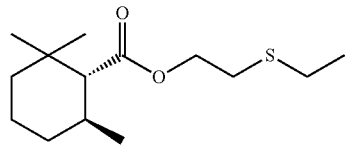 [SMILES: CCSCCOC(=O)[C@@H]1[C@@H](C)CCCC1(C)C]

To a cold flask containing the (1R,6S)-isomer of the acid chloride intermediate at 0° C., was added ethyl-2-hydroxyl ethylsulfide (10.5 eq; used as solvent) drop wise over 20 mins. After addition, the mixture was warmed to room temperature where it remained overnight. The material was diluted with ethyl acetate and washed with 5% Na$_2$CO$_3$ (1×) and water (1×). The aqueous layer was back extracted with ethyl acetate (1×). The organics were combined and washed with brine (1×). The organics were separated and dried over MgSO$_4$, filtered and concentrated under reduced pressure. The crude material was purified via silica gel elated with 0-5% Ethyl Acetate/Hexanes (57.7% yield). $^1$H NMR (400 MHz, CDCl$_3$) δ ppm 0.87 (m, 10H) 1.14 (ddd, 1H) 1.25 (t, 3H) 1.37 (m, 1H) 1.47 (m, 2H) 1.69 (m, 1H) 1.81 (m, 2H) 2.58 (m, 2H) 2.73 (m, 2H) 4.20 (m, 2H). $^{13}$C NMR (101 MHz, CDCl$_3$) δ ppm 14.91, 21.00, 21.24, 21.72, 26.23, 30.14, 30.25, 31.43, 34.56, 41.23, 60.86, 62.92, 174.43. Odor descriptors: weak, garlic.

Example 8: Synthesis of (1R,6S)-cyclopropylmethyl 2,2,6-trimethylcyclohexanecarboxylate

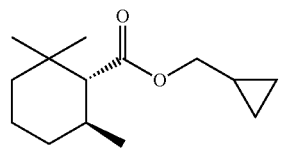 [SMILES: C[C@H]1CCCC(C)(C)[C@@H]1C(=O)OCC1CC1]

To a cold flask containing the (1R,6S)-isomer of the acid chloride intermediate at 0° C., was added cyclopropanemethanol (10.5 eq; used as solvent) drop wise over 20 mins. After addition, the mixture was warmed to room temperature where it remained overnight. The material was diluted with ethyl acetate and washed with 5% Na$_2$CO$_3$ (1×) and water (1×). The aqueous layer was back extracted with ethyl acetate (1×). The organics were combined and washed with brine (1×). The organics were separated and dried over MgSO$_4$, filtered and concentrated under reduced pressure. The crude material was purified via silica gel eluted with 0-2% Ethyl Acetate/Hexanes (32.0% yield). $^1$H NMR (400 MHz, CDCl$_3$) δ ppm 0.25 (m, 2H) 0.53 (m, 2H) 0.87 (m, 10H) 1.13 (m, 2H) 1.37 (m, 1H) 1.48 (m, 2H) 1.69 (m, 1H) 1.81 (m, 2H) 3.87 (m, 2H). $^{13}$C NMR (101 MHz, CDCl$_3$) δ ppm 3.44, 10.09, 20.93, 21.24, 21.77, 30.28, 31.36, 34.61, 41.31, 60.92, 68.45, 174.69. Odor descriptors: floral, fruity, red berry.

Example 9: Synthesis of (1R,6S)-tert-butyl 2,2,6-trimethylcyclohexanecarboxylate

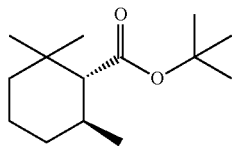 [SMILES: C[C@H]1CCCC(C)(C)[C@@H]1C(=O)OC(C)(C)C]

To a cold flask containing the (1R,6S)-isomer of the acid chloride intermediate at 0° C., was added tert-butanol (10.5 eq; used as solvent) drop wise over 20 mins. After addition, the mixture was warmed to room temperature where it remained overnight. The material was diluted with ethyl acetate and washed with 5% $Na_2CO_3$ (1×) and water (1×). The aqueous layer was back extracted with ethyl acetate (1×). The organics were combined and washed with brine (1×). The organics were separated and dried over $MgSO_4$, filtered and concentrated under reduced pressure. The crude material was purified via silica gel eluted with 0-2% Ethyl Acetate/Hexanes (39.5% yield). $^1$H NMR (400 MHz, $CDCl_3$) δ ppm 0.89 (m, 10H) 1.10 (m, 1H) 1.34 (m, 1H) 1.45 (m, 11H) 1.65 (m, 2H) 1.79 (m, 1H). $^{13}$C NMR (101 MHz, $CDCl_3$) δ ppm 20.81, 21.28, 21.80, 28.28, 30.30, 31.36, 34.66, 41.47, 61.58, 79.82, 173.95. Odor descriptors: floral, rose, fruity, apple.

Example 10: Synthesis of (1R,6S)-cyclopentyl 2,2,6-trimethylcyclohexanecarboxylate

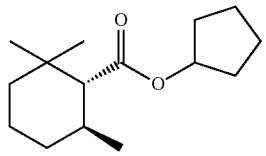 [SMILES: C[C@H]1CCCC(C)(C)[C@@H]1C(=O)OC1CCCC1]

To a cold flask containing the (1R,6S)-isomer of the acid chloride intermediate at 0° C., was added cyclopentanol (10.5 eq; used as solvent) drop wise over 20 mins. After addition, the mixture was warmed to room temperature where it remained overnight. The material was diluted with ethyl acetate and washed with 5% $Na_2CO_3$ (1×) and water (1×). The aqueous layer was back extracted with ethyl acetate (1×). The organics were combined and washed with brine (1×). The organics were separated and dried over $MgSO_4$, filtered and concentrated under reduced pressure. The crude material was purified via silica gel eluted with 0-1% Ethyl Acetate/Hexanes (59.7% yield). $^1$H NMR (400 MHz, $CDCl_3$) δ ppm 0.86 (m, 10H) 1.13 (ddd, 1H) 1.36 (m, 1H) 1.47 (m, 2H) 1.57 (m, 2H) 1.74 (m, 9H) 5.16 (tt, 1H). $^{13}$C NMR (101 MHz, $CDCl_3$) δ ppm 20.85, 21.28, 21.78, 23.74, 30.23, 31.30, 32.75, 33.39, 34.65, 41.40, 60.94, 174.33. Odor descriptors: weak, pineapple, apple, tropical fruity, peach.

Example 11: Fragrance Composition

The composition presented in Table 1 provided a rose fruit women's cologne. "TEC" is triethyl citrate. "DPG" is dipropylene glycol.

TABLE 1

| Component | Parts per thousand |
|---|---|
| Methyl 3-oxo-2-pentylcyclopentaneacetate | 200.0 |
| 1,3,4,6,7,8-Hexahydro-4,6,6,7,8,8-hexamethyl-cyclopenta(g)-2-benzopyran 50% in DPG | 160.0 |
| Phenethyl alcohol | 110.0 |
| Ionone, beta | 80.0 |
| Citronellol | 75.0 |
| ORBITONE ® 1-(1,2,3,4,5,6,7,8-octahydro-2,3,8,8-tetramethyl-2-naphthalenyl)-ethanone | 70.0 |
| 4-Methyl-2-(2-methylpropyl)oxan-4-ol | 60.0 |
| Geraniol pure | 40.0 |
| Linalool syn | 20.0 |
| 16-Oxacyclohexadecan-1-one | 20.0 |
| 2-Phenoxyethyl isobutyrate | 18.0 |
| Phenylethyl 2-methylbutyrate | 15.0 |
| HINDINOL ® (2-Methyl-4-[(1R)-2,2,3-trimethyl-3-cyclopenten-1-yl]-(2E)-buten-1-ol) | 15.0 |
| MUSK T ® (1,4-Dioxacycloheptadecane-5,17-dione) | 12.0 |
| (1R,6S)-Allyl 2,2,6-trimethylcyclohexane-carboxylate | 10.0 |
| Bergamot oil | 10.0 |
| Vanillin | 7.5 |
| 3-(1,3-Benzodioxol-5-yl)-2-methylpropanal | 6.0 |
| 4-(4-Hydroxyphenyl)butan-2-one | 6.0 |
| Nonalactone, gamma | 6.0 |
| Diethyl malonate | 5.0 |
| Undecalactone, gamma | 5.0 |
| (3aR,5aS,9aS,9bR)-3a,6,6,9a-Tetramethyl-2,4,5,5a,7,8,9,9b-octahydro-1H-benzo[e][1]benzofuran | 4.5 |
| n-Hexyl acetate | 4.0 |
| Hexyl 2-methylbutyrate | 3.5 |
| Allyl cyclohexylpropionate | 3.0 |
| Allyl heptoate | 3.0 |
| Ethyl isobutyrate | 3.0 |
| Ethyl 2-methylbutyrate) | 3.0 |
| (5E)-3-Methylcyclopentadec-5-en-1-one | 3.0 |
| Eugenol | 2.5 |
| 4-Methylphenylacetaldehyde 50% @1% in TEC | 2.0 |
| n-Decanal 10% in DPG | 2.0 |
| 2-Ethyl-3-hydroxypyran-4-one | 2.0 |
| 2,5,5-trimethyl-1,3,4,4a,6,7-hexahydronaphthalen-2-ol | 1.5 |
| (Z)-4-methyl-2-(2-methylprop-1-enyl)oxane | 1.0 |
| Cis-3-Hexenyl acetate | 0.5 |
| Ethyl 2-methylpentanoate | 0.5 |
| Violet T (Carbonic acid, 4-cycloocten-1-yl methyl ester) | 0.5 |

Example 12: Flavor Composition

The composition presented in Table 2 provided a flavor composition usable in a toothpaste:

TABLE 2

| Component | Parts per hundred |
|---|---|
| Alpha pinene | 1.40 |
| Beta pinene | 1.60 |
| Menthyl acetate | 6.00 |
| Menthone | 20.00 |
| Isomenthone | 10.00 |
| Menthol | 59.90 |
| Eucalyptol | 1.00 |
| (1R,6S)-allyl 2,2,6-trimethylcyclohexane-carboxylate | 0.10 |

Example 13: Fragrance Composition

The composition presented in Table 3 provided a fragrance composition usable in a pineapple rose scented candle:

TABLE 3

| Component | Parts per ten thousand |
|---|---|
| Phenethyl alcohol | 1400.0 |
| Methyl dioxolane | 1200.0 |
| Benzyl benzoate | 1000.0 |
| Methyl 3-oxo-2-pentylcyclopentaneacetate | 900.0 |
| Linalool syn | 750.0 |
| Citronellol | 700.0 |
| Ally cyclohexyl propionate | 700.0 |
| Allyl heptoate | 500.0 |
| 2-Phenoxyethyl isobutyrate | 450.0 |
| Ethyl caproate | 340.0 |
| Allyl phenoxyacetate | 300.0 |
| 1-Citronellyl propionate | 250.0 |
| Phenylethyl 2-methylbutyrate | 180.0 |
| Prenyl acetate | 160.0 |
| Hexyl caproate | 130.0 |
| Undecalactone, gamma | 90.0 |
| Ethyl caprylate | 80.0 |
| 2-Ethyl-3-hydroxypyran-4-one | 70.0 |
| Furaneol | 50.0 |
| Orange oil | 40.0 |
| Ethyl butyrate | 40.0 |
| 1-(2,6,6-trimethyl-1-cyclohex-2-enyl)hepta-1,6-dien-3-one | 40.0 |
| Violet T (Carbonic acid, 4-cycloocten-1-yl methyl ester) | 30.0 |
| Cis-3-hexenyl acetate) | 30.0 |
| Phenylethyl acetate | 20.0 |
| Citral syn refined | 20.0 |
| Methyl caprylate | 10.0 |
| Propyl caproate | 10.0 |
| (Z)-4-methyl-2-(2-methylprop-1-enyl)oxane | 10.0 |
| (1R,6S)-Allyl 2,2,6-trimethylcyclohexane-carboxylate | 500.0 |

The composition of Table 3 provided a rich fresh yellow fruit fragrance, with pineapple radiance and a hint of green. Inclusion of 5% (500.0 parts per ten thousand) (1R,6S)-allyl 2,2,6-trimethylcyclohexane-carboxylate in the composition of Table 3 was important to the composition's fragrance. Replacement of (1R,6S)-allyl 2,2,6-trimethylcyclohexane-carboxylate with 5% benzyl benzoate provided a composition with a solvent-like odor and a fragrance that was flat and lacking richness and diffusion. Replacement of (1R,6S)-allyl 2,2,6-trimethylcyclohexane-carboxylate with 5% delta-damascone provided a composition with a strong, very floral rosy plum and ripe red fruit fragrance, with less freshness than the composition of Table 3. Replacement of (1R,6S)-allyl 2,2,6-trimethylcyclohexane-carboxylate with 5% THESARON® ((1R,6S)-ethyl 2,2,6-trimethylcyclohexane-carboxylate) provided a composition with a fragrance that was fruity, rosy, less sweet, drier, and not so ripe as the composition of Table 3.

Example 14: Flavor Composition

The composition presented in Table 4 provided a flavor composition usable in a mouthwash, e.g., at a concentration of about 0.1% to about 0.3%, by weight.

TABLE 4

| Component | Parts per hundred |
|---|---|
| Menthol | 59.00 |
| Anethole | 10.00 |
| Menthone | 10.00 |
| Isomenthone | 5.00 |
| (1S,6R)-allyl 2,2,6-trimethylcyclohexanecarboxylate | 5.00 |
| l-Limonene | 4.00 |
| Menthyl Acetate | 3.00 |
| Eucalyptol | 1.50 |
| Methyl Salicylate | 1.00 |
| Beta Pinene | 0.80 |
| Alpha Pinene | 0.70 |

Example 15: Bleach Stability Testing

Hypochlorite stability testing of (1R,6S)-allyl 2,2,6-trimethylcyclohexane-carboxylate and delta-damascone was conducted according to the following procedures.

A commercial sodium hypochlorite bleach product, CLOROX® Concentrated Bleach—Unscented, was obtained. The product is a light yellow aqueous solution and typically contains approximately 4.0% to 5.0% NaClO, by weight, and a sufficient amount of sodium hydroxide to create a pH in a range from about 12.4 to about 12.7.

The NaClO content of the CLOROX® Concentrated Bleach—Unscented as well as the NaClO content of all of the samples tested below was measured according to the following procedure. The sample to be analyzed was first thoroughly mixed. Then, 2 g of sample was weighed for analysis into a 250 ml Erlenmeyer flask. Subsequently, 15 mL of 10% KI (potassium iodide) and 5 mL of $H_2SO_4$ 2.5M were added to flask, and the resulting mixture was stirred thoroughly. Free iodine was then titrated with 0.1 N sodium thiosulfate until yellow color disappeared, and the volume of sodium thiosulfate solution added was recorded.

Calculations: Weight % NaClO=((volume sodium thiosulfate, in mL)×(normality of sodium thiosulfate solution)×37.22×100)÷(Sample weight, in grams×1000).

The initial concentration (weight %) of NaClO in the CLOROX® Concentrated Bleach—Unscented was determined to be 4.57% according to the above procedure.

Sixty (60) gram samples of (1R,6S)-allyl 2,2,6-trimethylcyclohexane-carboxylate and delta-damascone were added to the CLOROX® Concentrated Bleach—Unscented in HDPE bottles. The compounds were allowed to float on top of the bleach solution. Control samples of the CLOROX® Concentrated Bleach—Unscented free of any added flavor or fragrance compounds were also prepared. One set of samples was held at room temperature ("RT," approximately 21° C.) while another set of samples was held at 38° C. Both sets of samples were tested for odor and stability at two (2) weeks and four (4) weeks. Odor was determined according to a six-tier qualitative ranking system: 1+=Excellent, 1=Very Good, 2=Good, 3=Fair, 4=Poor, and 5=Unacceptable. Stability was measured by determining NaClO concentration (weight %) according to the above procedure. The results of testing are shown in Tables 5 and 6.

TABLE 5

| | Odor Testing. | | | |
|---|---|---|---|---|
| | Odor at 2 weeks | | Odor at 4 weeks | |
| Sample: | RT | 38° C. | RT | 38° C. |
| Control (unperfumed) | — | — | — | — |
| (1R,6S)-allyl 2,2,6-trimethylcyclohexane-carboxylate | 2 | 3 | 3 | 4 |
| delta-damascone | 3 | 4 | 4 | 4 |

TABLE 6

| Sample: | Stability Testing. | | | | | | | |
| --- | --- | --- | --- | --- | --- | --- | --- | --- |
| | 2 weeks - Concentration of NaClO (weight %) | | 4 weeks - Concentration of NaClO (weight %) | | 2 weeks - Percentage of NaClO degraded | | 4 weeks - Percentage of NaClO degraded | |
| | RT | 38 °C. | RT | 38 °C. | RT | 38 °C. | RT | 38 °C. |
| Control (unperfumed) | 4.39 | 4.12 | 4.22 | 3.74 | 3.96 | 9.87 | 7.68 | 18.18 |
| (1R,6S)-allyl 2,2,6-trimethylcyclohex-ane-carboxylate | 4.29 | 3.99 | 4.14 | 3.47 | 6.15 | 12.80 | 9.45 | 24.02 |
| delta-damascone | 4.27 | 3.59 | 3.91 | 3.19 | 6.63 | 21.44 | 14.44 | 30.32 |

The data of Table 6 indicates that (1R,6S)-allyl 2,2,6-trimethylcyclohexane-carboxylate can have improved stability to sodium hypochlorite bleach as compared to delta-damascone. Reduced degradation of NaClO was observed in samples containing (1R,6S)-allyl 2,2,6-trimethylcyclohexane-carboxylate as compared to samples containing delta-damascone. After 4 weeks at room temperature, 9.45% of NaClO in the sample of bleach containing (1R,6S)-allyl 2,2,6-trimethylcyclohexane-carboxylate had degraded, as compared to 14.44% of NaClO in the sample of bleach containing delta-damascone. After 4 weeks at 38° C., 24.02% of NaClO in the sample of bleach containing (1R,6S)-allyl 2,2,6-trimethylcyclohexane-carboxylate had degraded, as compared to 30.32% of NaClO in the sample of bleach containing delta-damascone.

What is claimed is:

1. A compound of Formula (I):

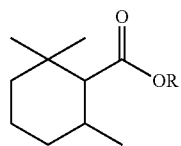

(I)

or a stereoisomer or mixture thereof, wherein:
R is an unsubstituted or substituted C4-C8 branched chain alkyl, an unsubstituted or substituted C3-C8 straight chain alkenyl, an unsubstituted or substituted C3-C8 branched chain alkenyl, an unsubstituted or substituted C3-C8 straight chain alkynyl, an unsubstituted or substituted C3-C8 branched chain alkynyl, an unsubstituted or substituted C3-C8 cycloalkyl, an unsubstituted or substituted C3-C8 cycloalkenyl, an unsubstituted or substituted C2-C8 alkylalkoxy, an unsubstituted or substituted C2-C8 alkyl(alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C1-C8 acyl, or an unsubstituted or substituted carboxy; with the proviso that R is not tert-butyl.

2. A compound of Formula (Ib):

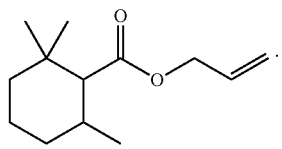

(Ib)

3. A compound of (1R,6S)-allyl 2,2,6-trimethylcyclohexanecarboxylate with the following Formula:

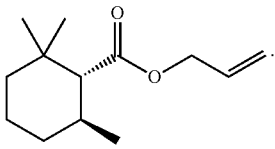

4. A compound of Formula (Ic):

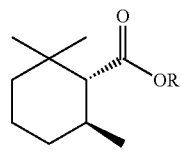

(Ic)

or a stereoisomer or mixture thereof, wherein:
R is an unsubstituted or substituted C4-C8 branched chain alkyl, an unsubstituted or substituted C3-C8 straight chain alkenyl, an unsubstituted or substituted C3-C8 branched chain alkenyl, an unsubstituted or substituted C3-C8 straight chain alkynyl, an unsubstituted or substituted C3-C8 branched chain alkynyl, an unsubstituted or substituted C3-C8 cycloalkyl, an unsubstituted or substituted C3-C8 cycloalkenyl, an unsubstituted or substituted C2-C8 alkylalkoxy, an unsubstituted or substituted C2-C8 alkyl(alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C1-C8 acyl, or an unsubstituted or substituted carboxy.

5. A compound of Formula (Id):

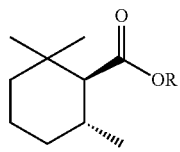

(Id)

or a stereoisomer or mixture thereof, wherein:
R is an unsubstituted or substituted C4-C8 branched chain alkyl, an unsubstituted or substituted C3-C8 straight chain alkenyl, an unsubstituted or substituted C3-C8 branched chain alkenyl, an unsubstituted or substituted C3-C8 straight chain alkynyl, an unsubstituted or substituted C3-C8 branched chain alkynyl, an unsubstituted or substituted C3-C8 cycloalkyl, an unsubstituted or substituted C3-C8 cycloalkenyl, an unsubstituted or substituted C2-C8 alkylalkoxy, an unsubstituted or substituted C2-C8 alkyl(alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C1-C8 acyl, or an unsubstituted or substituted carboxy.

6. A flavor composition comprising:
a. one or more compounds of Formula (I):

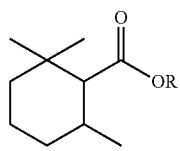

(I)

or a stereoisomer or mixture thereof wherein:
R is an unsubstituted or substituted C4-C8 branched chain alkyl, an unsubstituted or substituted C3-C8 straight chain alkenyl, an unsubstituted or substituted C3-C8 branched chain alkenyl, an unsubstituted or substituted C3-C8 straight chain alkynyl, an unsubstituted or substituted C3-C8 branched chain alkynyl, an unsubstituted or substituted C3-C8 cycloalkyl, an unsubstituted or substituted C3-C8 cycloalkenyl, an unsubstituted or substituted C2-C8 alkylalkoxy, an unsubstituted or substituted C2-C8 alkyl(alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C1-C8 acyl, or an unsubstituted or substituted carboxy; and
b. one or more additional flavor components.

7. The flavor composition of claim 6, wherein the compound of Formula (I) is (1R,6S)-allyl 2,2,6-trimethylcyclohexanecarboxylate.

8. The flavor composition of claim 6 or claim 7, wherein the flavor composition is incorporated into a product selected from the group consisting of foods, beverages, confectionaries, oral care products, pharmaceuticals, and gelatinous materials.

9. The flavor composition of claim 8, wherein the product is a beverage selected from the group consisting of alcoholic beverages, soft drinks, juices, teas, and flavored waters.

10. The flavor composition of claim 8, wherein the product is a confectionary selected from the group consisting of candies and gums.

11. The flavor composition of claim 8, wherein the product is an oral care product selected from the group consisting of toothpastes and mouthwashes.

12. A fragrance composition comprising:
a. one or more compounds of Formula (I):

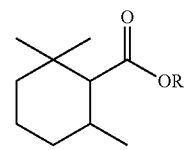

(I)

or a stereoisomer or mixture thereof, wherein:
R is an unsubstituted or substituted C4-C8 branched chain alkyl, an unsubstituted or substituted C3-C8 straight chain alkenyl, an unsubstituted or substituted C3-C8 branched chain alkenyl, an unsubstituted or substituted C3-C8 straight chain alkynyl, an unsubstituted or substituted C3-C8 branched chain alkynyl, an unsubstituted or substituted C3-C8 cycloalkyl, an unsubstituted or substituted C3-C8 cycloalkenyl, an unsubstituted or substituted C2-C8 alkylalkoxy, an unsubstituted or substituted C2-C8 alkyl(alkylthio), an unsubstituted or substituted aryl, an unsubstituted or substituted benzyl, an unsubstituted or substituted nonaromatic heterocyclic, an unsubstituted or substituted heteroaryl, an unsubstituted or substituted C1-C8 acyl, or an unsubstituted or substituted carboxy; and
b. one or more additional fragrance components.

13. The fragrance composition of claim 12, wherein the compound of Formula (I) is (1R,6S)-allyl 2,2,6-trimethylcyclohexanecarboxylate.

14. The fragrance composition of claim 12 or claim 13, wherein the flavor composition is incorporated into a product selected from the group consisting of perfumes, colognes, air fresheners, candles, personal care products, cosmetics, detergents, fabric care products, and household cleaning agents.

15. The fragrance composition of claim 14, wherein the product is a personal care product selected from the group consisting of soaps, deodorants, shampoos, conditioners, shower gels, and shaving lotions.

16. The fragrance composition of claim 14, wherein the product is a cosmetic selected from the group consisting of creams, lotions, ointments, oils, sprays, powders, gels, polishes, and lipsticks.

17. A flavor composition comprising:
a. a compound of the following Formula:

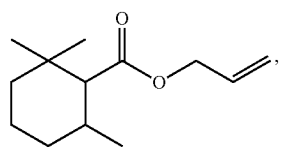

and
b. one or more additional flavor components.

18. A fragrance composition comprising:
a. a compound of the following Formula:
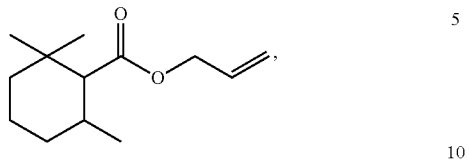
and
b. one or more additional fragrance components.
* * * * *